United States Patent [19]

Case et al.

[11] Patent Number: 5,957,868
[45] Date of Patent: Sep. 28, 1999

[54] SURFACE CONTOUR MEASUREMENT INSTRUMENT

[75] Inventors: James Ralph Case, Brackney, Pa.; Joseph Duane Kulesza, Binghamton, N.Y.

[73] Assignee: International Business Machines Corporation, Armonk, N.Y.

[21] Appl. No.: 09/087,593

[22] Filed: May 29, 1998

Related U.S. Application Data

[62] Division of application No. 08/650,501, May 20, 1996, Pat. No. 5,865,789.

[51] Int. Cl.$^6$ .................................................. A61B 5/103
[52] U.S. Cl. ........................ 600/587; 600/590; 600/595; 433/214; 33/514; 33/551
[58] Field of Search ................................. 600/587, 590, 600/595; 433/68, 213, 214, 215; 364/474.03, 474.37, 560; 33/511, 556, 557, 558, 559, 560, 561, 561.1, 514, 551

[56] References Cited

U.S. PATENT DOCUMENTS

| | | |
|---|---|---|
| 4,182,312 | 1/1980 | Mushabac . |
| 4,400,884 | 8/1983 | Baresh et al. . |
| 4,611,288 | 9/1986 | Duret et al. . |
| 4,691,715 | 9/1987 | Tanne . |
| 4,742,464 | 5/1988 | Duret et al. . |
| 4,876,758 | 10/1989 | Rolloff et al. . |
| 4,890,235 | 12/1989 | Reger et al. . |
| 4,935,635 | 6/1990 | O'Harra . |
| 4,972,351 | 11/1990 | Reger ...................................... 364/468 |
| 4,997,369 | 3/1991 | Shafir . |
| 4,998,354 | 3/1991 | Silverman et al. . |
| 5,088,503 | 2/1992 | Seitz ........................................ 600/592 |
| 5,257,184 | 10/1993 | Mushabac . |
| 5,359,511 | 10/1994 | Schroeder . |
| 5,497,336 | 3/1996 | Anderson . |

*Primary Examiner*—Richard J. Apley
*Assistant Examiner*—William LaMarca
*Attorney, Agent, or Firm*—Schmeiser, Olsen & Watts; Lawrence R. Fraley

[57] ABSTRACT

Back-to back hydraulically linked pistons are mechanically coupled to contact probes and measurement sensors. The pistons are hydraulically linked by small diameter flexible conduits which enable the contact probes and the measurement sensors to be mounted and moved independently of each other without affecting the ability of the measurement instrument to simultaneously measure a plurality of points on a selected predefined surface, such as a human tooth. The present invention overcomes the problems associated with the complex mechanical linkages heretofore required in such instruments.

4 Claims, 2 Drawing Sheets

SURFACE CONTOUR MEASUREMENT INSTRUMENT

This application is a divisional of U.S. application Ser. No. 08/650,501, filed May 20, 1996, now U.S. Pat. No. 5,865,789.

BACKGROUND OF TEE INVENTION

1. Technical Field

This invention relates generally to multi point measuring instruments, and more particularly to a measuring instrument having a plurality of probes disposed in a compact, easily maneuverable support member.

2. Background Art

Multi point measurement instruments are typically used to measure the contour of relatively small objects, such as teeth. For example, it is desirable to accurately identify the shape of a ground tooth prior to fitting a crown over the tooth. Also, it is often desirable to inspect relatively small articles of manufacture to assure correct three-dimensional alignment and relative tolerances of particular features of the article. U.S. Pat. No. 4,997,369 issued Mar. 5, 1991 to Aaron Shafir describes a probe that is movable along three independent axes. In order to obtain the plural measurements necessary to describe a surface contour, the probe must be moved after each independent measurement, the position data recorded, and the probe moved to the next position whereat the procedure is repeated. This process is cumbersome, time consuming and subject to error if the anchor point of the apparatus is inadvertently moved during the measurement process.

More recently, U.S. Pat. No. 5,257,184 was issued Oct. 26, 1993 to David Mushubac for a device capable of taking measurements which provide a cross-sectional outline of a human tooth. The Mushubac device uses a plurality of stylus elements, additional components for establishing a reference position, and various means for measuring the displacement of the styli along respective axes. The Mushubac instrument is very complex and requires considerable skill and training in order to assure accurate data measurements. Also, the large number of relatively fragile precision components make the instrument costly to manufacture and difficult to calibrate, repair and maintain.

In other surface contour measuring devices, spring-loaded levers are arranged in an arcuate pattern about the tooth and extend outwardly from the patient's mouth to a pivot point. The outward ends of the levers are connected to light-optic bundles or other measurement device, such as LVDTs or glass encoders, which track and amplify the displacement of the contact tip. It has been found that mechanical-linkage devices for measuring surface contours have a number of inherent problems. For example, each of the spring-loaded levers typically have a different angle of approach to the tooth surface which must be maintained from the contact point to the view, or measurement, plane of the device. The view, or measurement, plane is generally a mechanically amplified plane provided by the ends of levers opposite the contact end, providing an enlarged cross-sectional representation of the actual tooth surface. Each of the levers must wrap around the hand of the operator holding the device to provide a view plane behind the operator's hand. The direction of displacement at the probe end of the lever must be duplicated at the view plane, requiring that each lever have at least three pivotable segments which rotate about separate pivot points, and a requirement for interconnecting linkage between the segments. This arrangement makes it difficult to maintain accurate simultaneous translation of all of the segments of all of the levers, thereby affecting the accuracy of the measurements. Furthermore, mechanical-linkage measurement devices are cumbersome to use, prone to erroneous readings if not held steady during the measurement process, and may appear threatening to the patient on which the instruments are used.

The present invention is directed to overcoming the problems set forth above. It is desirable to have a multi point measurement instrument for small articles such as teeth, that does not require fixed mechanical linkage between the contact probe and the measurement, or readout, components of the instrument. It is also desirable to have such an instrument that is compact, easy to use, and has a flexible linkage between the probe support and the measurement components of the instrument. It is also desirable to have such an instrument wherein the probe support and measurement components are separately replaceable and interchangeable with different probe support configurations and measurement devices.

SUMMARY OF THE INVENTION

In one aspect of the present invention, a surface contour measurement instrument has a plurality of elongated probes each of which is attached to a first piston that is movably disposed in a respective fluid chamber provided in a probe support member. The measurement instrument also has a plurality of linear position sensors, each of which are mechanically linked to a second piston that is movably disposed in a respective fluid chamber provided in a measurement manifold. A plurality of flexible conduits extend between the respective fluid chambers in the probe support member and the measurement manifold. The surface contour measurement instrument also includes a means for biasing the distal end of each of the probes in a direction away from the probe support member, and a means for selectively moving the distal end of each of the probes to a retracted position in close proximity to the probe support member.

Other features of the surface contour measurement instrument embodying the present invention include the linear position sensors being linear variable-differential transformers having a movable armature attached to a respective one of the second pistons, and the means for biasing the distal end of each of the probes in a direction away from the probe support member includes a spring member operatively attached to each of the second piston members.

DETAILED DESCRIPTION OF A PRESENTLY PREFERRED EXEMPLARY EMBODIMENT

Figure 2:
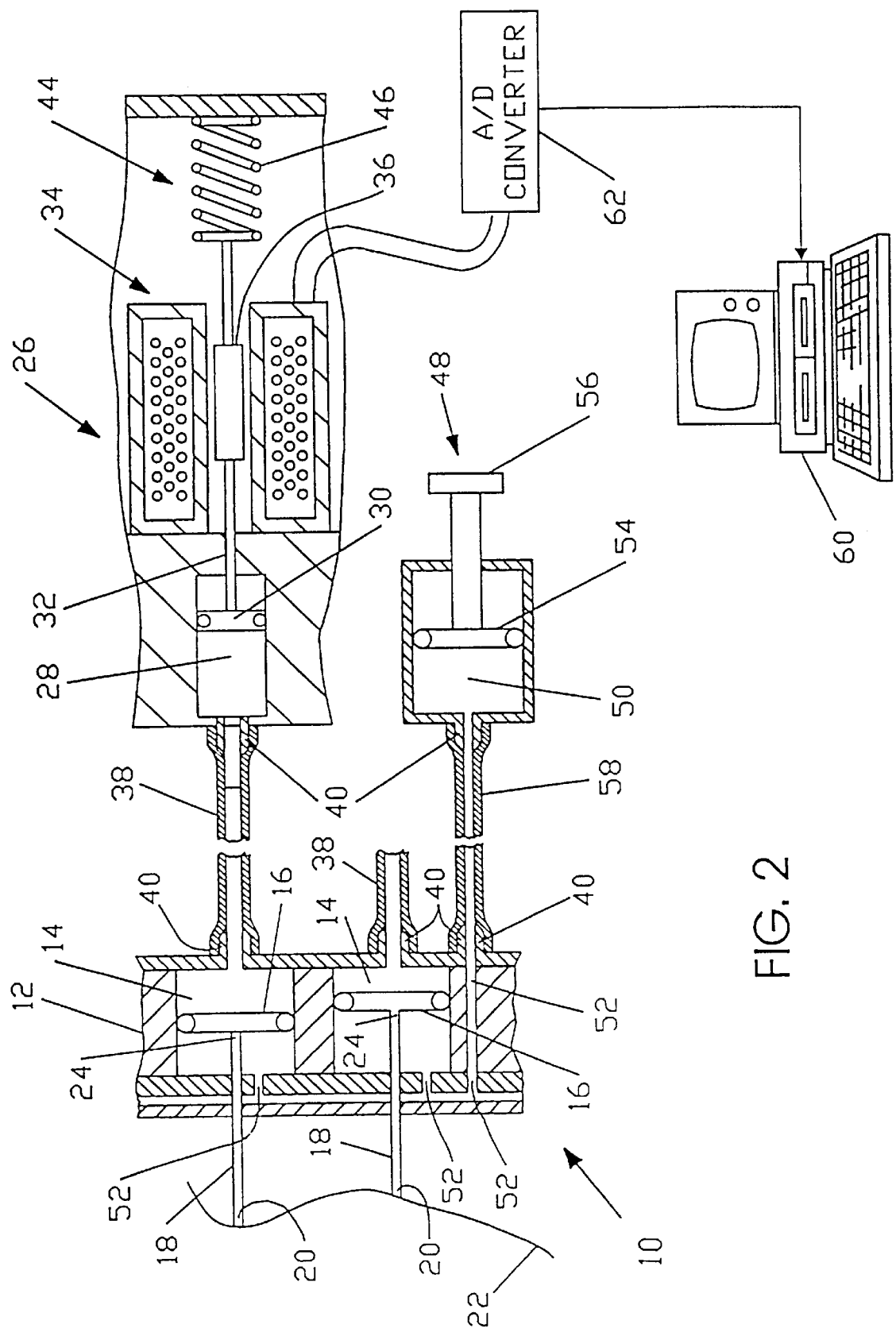
FIG. 2 is a schematic sectional view of a representative portion of the surface contour measuring instrument embodying the present invention.

In the preferred embodiment of the present invention, a surface contour measurement instrument 10 has a probe support member 12 that, as shown schematically in FIG. 2, has a plurality of predefined first fluid chambers 14 formed within the support member 12. A first piston member 16 is movably positioned in each of the first fluid chambers 14, and is positionable within the respective chamber, as is well known in the field of hydraulics, in response to the provision of a fluid pressure differential on opposite sides of the piston member 16. Preferably, the working fluid in the preferred embodiment of the present invention is a non-toxic fluid having relatively low viscosity characteristics, such as glycerine or mineral oil.

A plurality of elongated probes 18 are supported by the probe support member 12. Each of the probes 18 have a distal end 20 that extends outwardly from the support member 12 and is adapted, for example with a defined point or small diameter ball, for contact with a predefined surface 22, such as the surface of a human tooth. Each of the probes 18 also have a proximal end 24, spaced from the distal end 20 and positioned within a first fluid chamber 14 whereat it is connected to a respective one of the first piston members 16. The distal end 20 of each of the probes 18 is thus rigidly connected with a corresponding one of the first piston members 16 such that movement of one results is correlative movement of the other.

The surface contour measurement instrument 10 also has a measurement manifold 26 that has a plurality of predefined second fluid chambers 28 provided therein in like number as the first fluid chambers 14. A second piston member 30 is movably disposed in each of the second fluid chambers 28 and is mechanically linked, preferably by a rigid link 32, to a linear position sensor 34, such as a linear variable displacement transformer (LVDI), a glass encoder or other sensor arrangement capable of producing a signal indicative of the linear position, or displacement of the link-connected second piston member 30. In the preferred embodiment of the present invention, the linear position sensors 34 are conventional LVDTs which have a linearly movable armature 36 housed inside the coils of a differential transformer. As is well known, linear movement, or the linear position, of the armature 36 inside the coils affects the output voltage of the LVDT 34 by changing the inductance of the coils in equal but opposite amounts. Thus, the output voltage of LVDTs is very responsive to small changes in armature movement.

Importantly, each of the first fluid chambers 14 provided within the probe support member 12, is hydraulically connected to a corresponding one of the second fluid chambers 28 in the measurement manifold 26 by a flexible conduit 38 which in the preferred embodiment, is small diameter hypodermic tubing having high wall strength. Small diameter hypodermic tubing is highly flexible and can be bent around a very small radius without pinching or collapse.

Each of the first and second piston members 16,30 are sealed against the cylindrical wall of the first and second fluid chambers 14,28 in which they are respectively housed, by a conventional seal so that, in operation, the entire fluid volume between the first piston member 16 and the second piston member 30 is a defined constant volume. That is, a decease in fluid volume defined by the piston member in one chamber will cause a corresponding increase in the fluid volume of the other chamber. Thus, movement of the distal end 20 of the probe 18 will move the first piston member 16, resulting in a corresponding movement of the second piston member 30 and the linear position sensor 34 to which the second piston member 30 is attached by the link 32.

Mechanical gain, or amplification, of the linear displacement of the distal end 20 of the probes 18 may be conveniently provided, if so desired, by varying the radius ratio of the first piston members 16 and the first fluid chambers 14 with respect to the second piston members 30 and the second fluid chambers 28. Because, as described above, the fluid volume between the first piston member 16 and the second piston member 30 is a defined constant volume, and due to the incompressibility of the fluid medium, fluid is displaced from one fluid chamber must be equal to the fluid increase in the other chamber. Also, the change is displacement of one piston member with respect to the other is equal to the square of the difference in the respective radiuses of the two piston members which is also essentially equal to the radius of the fluid chamber r in which the piston is housed. The volume, v, of an enclosed cylindrical chamber is represented by the equation: $v=\pi r^2 h$, where h is the height of a cylinder such as the fluid chamber 14,28. Thus, it can be seen that if the radius of one of the paired piston members 16,30 and its respective fluid chamber 14,28 is changed, then the height h of the other fluid chamber and, accordingly, the resultant linear displacement of the other piston member, will change by a square factor. For example, if the radius r of one fluid chamber is changed by a factor of 2, the height h of the other chamber will change by a factor of 4, resulting in significant mechanical amplification of the displacement.

Because the output voltage of the LVDTs 34 is extremely sensitive to small changes in displacement, or position, of the cores, or armatures, 36, mechanical amplification i.e., differential diameters of the fluid chambers 14,28, is not required in the illustrated preferred embodiment of the present invention. However, in other measurement arrangements, such as optical viewing systems, it may be desirable to amplify the relatively small actual displacement of the distal end 20 of the probes 18.

Figure 1:
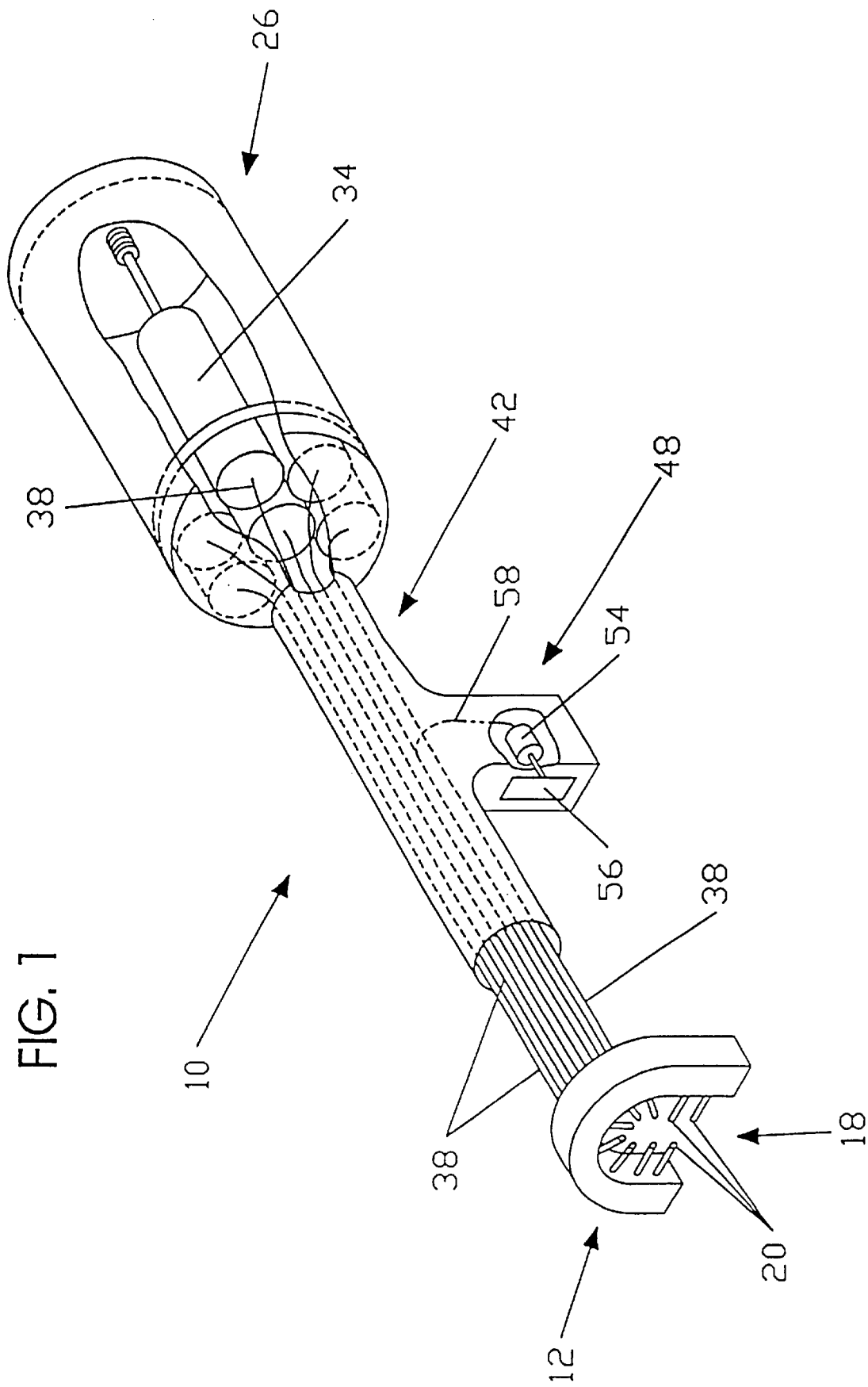
FIG. 1 is a schematic three-dimensional view of the surface contour measuring instrument embodying the present invention with portions of the outer case broken away to show otherwise hidden features.

The approach angle of each of the probes 18 with respect to the surface 22 to be measured, is determined by a guide support aperture machined in the wall of the probe support member 12, and may be different for each probe 18. For example, in the illustrative embodiment, the probe support member 12 is arcuately shaped and the probes 18 are arranged in a generally radially converging relationship with each other. When the probes 18 are extended, as illustrated in FIG. 1, the distal ends 20 are closely spaced together to provide a plurality of adjacent measurements of the surface contour of a relatively small solid object, such as a human tooth. In the illustrated embodiment, it can be seen that the length of travel, or displacement, of each probe 18 is limited by the height of the first fluid chambers 14 formed in the probe support member 12. For purposes of measuring the surface contour of human teeth, a travel length of only about 0.25 in (0.64 cm) is required. Thus, the probe support member 12 may be constructed so that it has a total thickness of less than 0.5 in (1.3 cm), enabling the support member 12 to be easily inserted into the mouth of a dental patient.

The probe support member 12 and the measurement manifold 26 are preferably provided with a means for removably connecting the flexible conduits 38 to the respective first and second fluid chambers 14,28 defined within the support member 12 and the measurement manifold 26. In the preferred embodiment, this connection is provided by small hollow nibs, or male connectors, 40 that communicate with an internal passageway between the nib 40 and a respective one of the internal fluid chambers 14,28. In this arrangement, the hypodermic tubing 38 is attached by pushing an end of the tubing 38 over the nib 40 which may also have appropriate barbs formed on an outer peripheral surface to further expand and retain the tubing 38. Alternatively, treaded or other types of separable connectors, such as quick-disconnect fittings, may also be used to removably connect the respective ends of the flexible conduits 38 to the probe support member 12 and the measurement manifold 26.

In the preferred embodiment of the present invention, the probe support member 12 may be conveniently formed of two or more components so that internal passageways can be more easily formed to provide the necessary fluid communication between the first fluid chambers 14 and the flexible conduit connectors 40. By judicious placement of the connectors 40 on an appropriate surface of the probe support member 12, the necessity of routing exposed tubing 38 over sharp edges can be avoided.

The structural components of the probe support member 12 may be either machined from a solid blank, cast and machined, or molded. Advantageously, since the probe support member 12 is separable from the measurement manifold 26, probe support members 12 adapted for specific measurement applications and having varying arrangements of probes 18 can be quickly interchanged and used with a single measurement manifold 26. Conversely, different measurement manifolds 26, for example a manifold equipped with fiber optics as described in the above-referenced U.S. Pat. No. 5,257,184, may be interchanged with an LVDT measurement manifold if direct visual recordation of a surface contour is desired.

Desirably, the flexible conduits 38 may be conveniently bundled together and supported by a handle assembly 42 that may also support the measurement manifold 26. The measurement manifold 42 may comprise individual measurement modules in which a second fluid chamber 28, containing a second piston member 30, is directly coupled to a linear position sensor 34, as schematically represented in FIG. 1, or may comprise a common structure with integrally formed second fluid chambers 28, each having a second piston member 30 linked to a sensor 34, as illustrated in FIG. 2.

The surface contour measurement instrument 10 also includes a means 44 for biasing the distal end 20 of each of the probes 18 to the extended position, i.e., in a direction away from the probe support member 12. In the preferred embodiment, as shown in FIGS. 1 and 2, the probe extension means 44 comprises a spring member 46 operatively attached to each of the second piston members 30 to urge the second piston member 30 in a direction which decreases the fluid capacity of the respective second fluid chamber 28 in which the second piston member 28 is housed. This action forces the hydraulically interconnected first piston member 16, and accordingly the attached probe 18, in a direction toward the surface 22 to be measured. Alternatively, the means 44 for biasing the distal end 20 of the probes 18 in the extended position may comprise an elastomeric member or pressurized source of fluid acting on the second piston members 30, to urge the second piston members 30 in a direction that would decrease the fluid capacity of the second fluid chambers 28 and increase the volume of the respectively interconnected first fluid chamber 1, thus bringing the distal ends 20 of the probes 18 into physical contact with the surface 22 to be measured.

The surface contour measurement instrument 10 comprising the present invention also includes a means 48 for selectively moving the distal end 20 of each of the probes 18 to a reset, or initial retracted, position at which the distal end 20 is in close proximity with the probe support member 12. In the preferred embodiment, the reset means 48 includes a source of fluid 50 that may be selectively directed to a predetermined portion of each of the first fluid chambers 14 by way of internally disposed interconnecting fluid passageways 52 formed within the probe support member 12. Preferably, the source of fluid 50 is a selectively volumetrically controllable chamber disposed within a hand-grip portion of the handle assembly 42 whose volume may be selectively varied by movement of a piston member 54 that is rigidly linked to a trigger 56 positioned externally of the grip. A single flexible conduit 58, also preferably formed of small-diameter hypodermic tubing, is routed through the handle assembly 42 and provides fluid communication between the chamber 50 and the interconnected fluid passageways 52 disposed in the probe support member 12. Thus, in response to an operator squeezing the trigger 56, fluid is pumped from the chamber 50, through the conduit 58 and interconnected fluid passageways 52, and into the outer end of each of first fluid chambers 14, causing the first piston members 16 to move to the right, as viewed in FIG. 2. This action causes the distal end 20 of each of the probes 18 to retract inwardly toward the support member 14. The decrease in volume in the right-hand portion of the first fluid chambers 14 causes fluid to flow from that portion of the first fluid chambers 14, through the flexible conduits 38, and into the second fluid chambers 28. The resultant increase in fluid volume within the second fluid chambers 28 causes the second piston members 30 to also retract and thereby position the linear position sensors 34 at an initial retracted, or reset, position.

Release of the trigger 56 will permit the distal ends 20 of the probes 18 to extend, under the bias force provided by the spring members 46, until they each respectively contact the predefined surface 22 of the tooth or other article being measured. Use of a hydraulically-connected trigger, without springs allows an operator to feel, or tactilely control, the force that is applied to the measurement surface 22 by distal ends 20 of the probes 18.

In the preferred embodiment, the output voltage of each of the LVDTs 34 is delivered to a programmable computer 60 whereat the linear position of the armature 36 is determined as a function of the output voltage. Typically, the analog output voltage signal of each of the LVDTs is converted to a digital value, either through a conventional analog to digital converter 62, or by an A/D conversion card provided in the internal hardware of the computer 60.

Typically, the surface contour measurement instrument 10 is calibrated with reference to a known dimensional block just before each use. During calibration the instrument 10 is adjusted for temperature or other variances that may affect the relative position of the distal end 20 of the probes 18 with respect to the position of the linear position sensor 34. Also, although not shown, in applications that may require frequent interchange of the probe support member 12, the measurement manifold 26, or other components of the measurement instrument, it may be desirable to provide a bleed vent in close proximity with the first fluid chambers 14 so that any entrapped air bubbles can be bled from the fluid system in much the same manner as air bubbles are conventionally bled from vehicular brake lines.

In an alternative embodiment, the means 44 for biasing the distal ends 20 of the probes 18 toward the measurement surface, and the means 48 for retracting the distal ends 20 of the probes 18 comprises a movable cylinder within a chamber that is in fluid communication with the outside, or right hand portion as viewed in FIG. 2, of each of the second fluid chambers 28. This arrangement obviates the need for the spring members 46 and the trigger reset actuator 56, and permits an operator to directly control the application the extension force on the contact probes 18 as well as the retract force to reset the probes 18 to an initial starting position.

Although the present invention is described in terms of a preferred exemplary embodiment and certain alternative arrangements, those skilled in the art will recognize that changes in probe construction and arrangement, in routing and arrangement of the flexible conduits, and in other known types of linear position sensors may be made, consistent with the specifically stated hydraulically connected probe and measurement piston arrangements, without departing from the spirit of the invention. Such changes are intended to fall within the scope of the following claims. Other aspects, features and advantages of the present invention can be obtained from a study of this disclosure, along with the appended claims.

What is claimed is:

1. A method for surface contour measurement, comprising the steps of:

provides a surface contour measurement instrument for accomplishing surface contour measurements with a mechanical contact mechanism that does not require a fixed mechanical linkage between a plurality of elongated sensing probes and fixed origin point of a predefined surface, the mechanical contact mechanism having a plurality of first chambers operationally linked to said plurality of elongated sensing probes, said plurality of first chambers being linked to a plurality of second fluid chambers via a plurality of flexible conduits, said second chambers communicating input to a position data recording means;

moving the mechanical contact mechanism to a position on the predefined surface to be measured;

aligning the mechanical contact mechanism to the position on the predefined surface to be measured;

recording position data; and repeating the foregoing steps as desired.

2. A method for surface contour measurement, the method comprising the steps of:

providing a surface contour measurement instrument having a plurality of first and second fluid chambers interconnected by a plurality of flexible conduits, said second fluid chambers communicating input to a position data recording means, and a mechanical contact mechanism that includes the plurality of first fluid chambers and a plurality of elongated probes, wherein the surface contour measurement instrument does not require a fixed mechanical linkage attached between said plurality of elongated probes and a fixed origin point of a predefined surface to provide accurate measurement results;

moving the mechanical contact mechanism to a position on the predefined surface to be measured;

aligning the mechanical contact mechanism to the position on the predefined surface to be measured;

recording the position data; and repeating the foregoing steps as desired.

3. The method of claim 1, wherein each of the plurality of first chambers have a diameter that is greater than a diameter of each of the plurality of second chambers.

4. The method of claim 1, wherein the mechanical contact mechanism is arc-shaped.

* * * * *